United States Patent [19]

Tanabe et al.

[11] Patent Number: 4,788,218
[45] Date of Patent: Nov. 29, 1988

[54] 17 A β-HYDROXY-7 α-METHYL-D-HOMO-19-NORANDROST-4,16-DIENE-3-ONE AND THE 17-ESTERS THEREOF: METHODS OF PREPARATION AND USES

[75] Inventors: Masato Tanabe, Palo Alto; David F. Crowe, Yreka; George Detre; Peters, Richard H., both of San Jose; Mitchell A.g34 Avery, Palo Alto, all of Calif.

[73] Assignee: SRI International, Menlo Park, Calif.

[21] Appl. No.: 856,386

[22] Filed: Apr. 28, 1986

Related U.S. Application Data

[63] Continuation-in-part of Ser. No. 612,415, May 21, 1984, abandoned.

[51] Int. Cl.⁴ .................... C07C 69/34; C07C 49/727; A61K 31/23
[52] U.S. Cl. .................... 514/510; 260/410; 260/405.5; 260/408; 514/691; 560/1; 560/100; 560/105; 560/107; 560/122; 560/123; 560/124; 560/128; 560/220; 560/228; 560/257; 568/372
[58] Field of Search ............ 260/410 R, 410 S, 405.5, 260/408; 514/510, 690, 691; 560/100, 105, 107, 220, 228, 257, 1, 122, 123, 124, 128; 568/369, 372

[56] References Cited

U.S. PATENT DOCUMENTS

| | | | |
|---|---|---|---|
| 2,819,276 | 1/1958 | Mihina et al. | 260/397.4 |
| 3,278,528 | 10/1966 | Bowers et al. | 260/239.55 |
| 3,984,476 | 10/1976 | Furst et al. | 260/586 |
| 4,087,524 | 5/1978 | Grunwell et al. | 424/238 |
| 4,155,918 | 5/1979 | Furst et al. | 260/345.9 |
| 4,578,475 | 3/1986 | Furst | 548/126 |

FOREIGN PATENT DOCUMENTS

| | | |
|---|---|---|
| 7701872 | 2/1977 | Netherlands . |
| 606113 | 10/1978 | Switzerland . |
| 1564144 | 4/1980 | United Kingdom . |
| 1569221 | 6/1980 | United Kingdom . |

OTHER PUBLICATIONS

Physician's Desk Reference, 39th Ed. (1985), pp. 771–773.
Didolkar et al., International Journal of Andrology, vol. 5, (1982), pp. 413–424.
Lotz, W., Journal of Steroid Biochemistry, vol. 13, pp. 1261–1264 (1980).
R. Riley, Sexual Medicine Today, pp. 14–19, Jan. 1983.
C. Djerassi, Science, vol. 151, pp. 1055–1061, (1966).
D. J. Patanelli, (ed.) "Hormonal Control of Male Fertility", Dept. Health, Educ. & Wlf., Pub. NIH 78–1097 (1977), pp. i–iii, & 420.
F. Newmann et al., International Journal of Andrology, Supp. 2, pp. 147–154 (1978).
G. Pincus et al., Science, vol. 124, p. 890 (1956).
J. Rock et al., in Science, vol. 124, p. 891 ff (1956).
G. Pincus, The Control of Fertility, Academic Press, N.Y., N.Y.; pub. 1965, pp. vii–xvii & 360.

Primary Examiner—Michael L. Shippen
Attorney, Agent, or Firm—Ciotti & Murashige, Irell & Manella

[57] ABSTRACT

Novel compounds having the general formula:

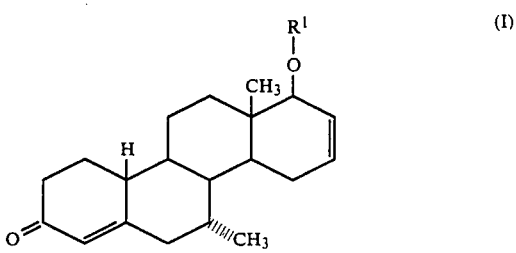

(I)

wherein:
$R^1$ is hydrogen or an acyl substituent of the formula:

$$-(C=O)-R^2$$

wherein:
$R^2$ is an alkyl, alkenyl, alkynyl, cycloalkyl, cycloalkylalkylene, haloalkyl, aryl, haloaryl or arylalkylene are described. These compounds have both gonadotropic and antigonadotropic properties depending upon the dosage level, and are therefore useful in therapy in the control of male fertility in mammals, particularly in human beings. These compounds combine gonadotropic, antigonadotropic and androgenic properties in the same compound. Their use with LHRH antagonists on male fertility control is also disclosed.

21 Claims, No Drawings

17 A β-HYDROXY-7 α-METHYL-D-HOMO-19-NORANDROST-4,16-DIENE-3-ONE AND THE 17-ESTERS THEREOF: METHODS OF PREPARATION AND USES

BACKGROUND OF THE INVENTION

The invention described herein was made in the course of work under a contract from the U.S. National Institutes of Health No. NO1-HD-0-2828 of the Department of Health and Human Resources.

This application is a continuation-in-part of U.S. patent application Ser. No. 612,415, filed May 21, 1984 which is now abandoned.

FIELD OF THE INVENTION

The present invention is in the field of steroid chemistry. More particularly, it concerns $17_a\beta$-hydroxy-7α-methyl-D-homo-19-norandrost-4,16-diene-3-one and its $17_a\beta$-hydroxy esters, their preparation and their use in the control of male fertility in mammals, particularly male human beings. These compounds combine gonadotropic, antigonadotropic and androgenic properties in the same compound and the effect can be selected based on the dose level.

RELATED ART

The use of substituted steroids for the control of conception in female mammals has been known for some time, see for example, G. Pincus et al. in *Science*, Vol. 124, p 890 (1956); J. Rock et al. in *Science*, Vol. 124, p 891 ff (1956); G. Pincus, *The Control of Fertility*, Academic Press, New York, N.Y., published in 1965; and C. Djerassi, *Science*, Vol. 151, p. 3716 (1966).

The lack of a similar contraceptive "pill" for males has stimulated research in male fertility control. Male fertility is a function of spermatogenesis. Since spermatogenesis is under hormonal control, the possibility of interfering with spermatogenesis by suppressing gonadotropins has been investigated, see for example, D. J. Patanelli (ed.) "Hormonal Control of Male Fertility" in Department of Health, Education and Welfare Publication, NIH 78-1097, Bethesda, Md., published in November 1977.

F. Newman et al., reported in the *International Journal of Andrology*, Supplement 2, pp 147–154, (1978), that the $\Delta^{16}$-D-homo-19-nortestosterone propionate was 50% as active as testosterone propionate as an androgen, and was 10 times as potent as testosterone propionate in decreasing testicular weight in rats when administered subcutaneously. Newman also reported, in contrast to the present invention, that all orally active androgens are 17-alkyl derivatives of testosterone. One such material, 17-methyltestosterone, is marketed by Brown Pharmaceutical Company. In the *Physician's Desk Reference*, 39th Ed (1985) it is disclosed that this 17-alkyl material has serious liver damaging side effects ranging from jaundice to benign liver cysts, and highly vascularized liver tumors which can lead to fatal hemorrhages. Thus, an alternative to these 17-alkyl testosterones would be desirable for oral androgen therapy.

Didolkar et al., in the *International Journal of Andrology*, Vol. 5, (1982) pp 413–424, compare antispermatogenic effects of a new D-homosteroid and testosterone in rabbits. They conclude that 18β-hydroxy-18α-methyl-16α,17α-methylene-D-homo-5α-androstane-3-one surpresses spermatogensis and increases accessory sex gland weights at doses when testosterone is still ineffective. Thus in rabbits, the new steroid appears to be a more potent androgen than testosterone but an association between antigonadotropic and androgenic properties is not observed.

W. Lotz in the *Journal of Steroid Biochemistry*, Vol. 13, pp 1261–1264, published in 1980 compares the tropic and serum leutinizing hormone (LH)-decreasing effects of testosterone, 19-nortestosterone, 5α-dihydrotestosterone and their corresponding D-homo-$\Delta^{16}$ analogs in rats. He concludes that the shape of the D ring is important for the ability of the 5α-reductase to act on these compounds. Further, 5α reduction at the 5-position is most important for the negative action on LH release, less important for tropic activity on accessory sex organs, and of minor importance for the myotropic (anabolic) activity.

Additional references which describe compounds which are either related to the structure of the compounds or the biological activity of the present invention include, R. Riley, *Sexual Medicine Today*, pp. 14–19, January 1983, and U.S. Pat. Nos. 2,819,276; 3,278,528; and 4,087,542, Republic of Germany Pat. No. 606,113 and Netherlands Pat. No. 7,701,872.

Oral androgen activity has also been reported by Segaloff for 7-methyl analogs of testosterone and 17-acyl esters of testosterone, compounds of different ring structure than the norandostrones of this invention.

Yet a further background point relates to U.S. Pat. Nos. 4,155,918 and 3,984,476 of Furst et al. These patents show generic structures which can include nor-steroids similar to the compounds of the present invention but in the case of the '918 materials having a 10 position methyl. These references disclose their materials to be useful as contraceptives and regulators of the female menstral cycle ('476) and as subquetaneous androgens (having 3 times the activity of testosterone which as will be shown the present materials are as much as 40 or more times as active as testosterone). Oral activity is not disclosed.

SUMMARY OF THE INVENTION

In one aspect this invention concerns steroid derivatives of the general formula:

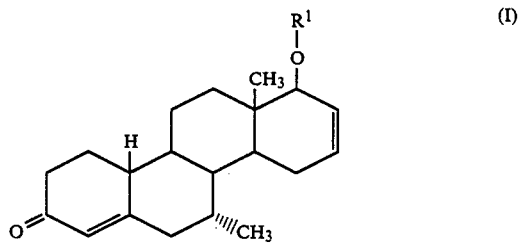

wherein:

R¹ is hydrogen or an acyl substituent of the formuls:

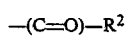

—(C=O)—R² wherein:

R² is an alkyl, alkenyl, alkynyl, cycloalkyl, cycloalkylalkylene, haloalkyl, aryl, haloaryl or arylalkylene.

These compounds can be administered orally and are useful in the control of male fertility and, at the same time, have androgenic activity. When so administered, they are potent androgens and depending on the dose, are either gonadotropic or antigonadotropic.

More importantly, they can be used as androgenic supplements to maintain male libido during male fertility control using LHRH antagonist. These uses and pharmaceutical formulations therefore constitute additional aspects of this invention. Other aspects of this invention include processes for preparation of the compounds of formula I and the novel intermediates thereof, as is described in more detail hereinbelow.

DETAILED DESCRIPTION OF THE INVENTION

The compounds of this invention are defined by the general formula I wherein $R^1$ is hydrogen or an acyl substituent of the formula, —(C=O)—$R^2$, wherein $R^2$ is an alkyl, alkenyl, alkynyl, cycloalkyl, cycloalkylalkylene, haloalkyl, aryl, haloaryl, or arylalkylene group.

As used herein:

"Acyl" refers to a group of the structure —(C=O)—$R^2$, where $R^2$ is as described herein. Acyl, therefore, includes such groups as, for example, acetyl, propanoyl (or propionyl), isopropanoyl, n-butanoyl (or n-butyryl), octanoyl, eicosanoyl, propenoyl (or acryloyl), 2-methylpropenoyl (or methacryloyl), octanoyl, tetradecenoyl, eicosenoyl, tetracosenoyl, propynoyl, n-butynoyl, i-butynoyl, n-2-octynoyl, n-2-tetradecynoyl, 2-chloropentanoyl, 2-chlorotetracosanyl, 3-bromo-2-methacryloyl, benzoyl, 1- and 2-naphthoyl, phenylacetyl, 6-phenylhexylenoyl, and the like.

"Alkenyl" refers to a branched or unbranched unsaturated hydrocarbon group of 2 to 24 carbon atoms and one or more unsaturated carbon-carbon bonds, such as for example, ethenyl, propenyl, isopropenyl, butenyl, isobutenyl, octenyl, decenyl, tetradecenyl, $\Delta^{8,11}$-heptadecadienyl, hexadecenyl, eicosenyl, tetracosenyl and the like.

"Alkyl" refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like.

"Alkylene" refers to a difunctional saturated branched or unbranched hydrocarbon chain containing from 1 to 6 carbon atoms, and includes, for example, methylene (—CH$_2$—), ethylene (—CH$_2$—CH$_2$—), propylene (—CH$_2$—CH$_2$—CH$_2$—), 2-methylpropylene [—CH$_2$—CH(CH$_3$)—CH$_2$—], hexylene [—(CH$_2$)$_6$—] and the like.

"Alkynyl" refers to a branched or unbranched acetylenically unsaturated hydrocarbon group of 2 to 24 carbon atoms such as ethynyl, 1-propynyl, 2-propylnyl, 1-butynyl, 2-butynyl, octynyl, decynyl, tetradecenyl, hexadecynyl, eicosynyl, tetracosynyl and the like.

"Aryl" refers to a phenyl or 1- or 2-naphthyl group. Optionally, these groups are substituted with one to four lower alkyl groups (having from one to six carbon atoms).

"Arylalkylene" refers to an aryl group as is defined herein which is attached to one end of an alkylene group as is defined herein. As used herein, the other end of the alkylene group is attached to the carbon of the carbonyl group to form the acyl group.

"Cycloalkyl" refers to a saturated hydrocarbon ring group having from 3 to 8 carbon atoms, and includes, for example, cyclopropyl, cyclobutyl, cyclohexyl, methylcyclohexyl, cyclooctyl, and the like.

"Cycloalkylalkylene" refers to a saturated hydrocarbon containing a cycloalkyl group as is defined herein and an alkylene group as is defined herein. The term includes for example cyclopropylmethylene, cyclobutylethylene, 3-cyclohexyl-2-methylpropylene, 6-cyclooctyl)hexylene, and the like.

"Halo" or "halogen" refers to fluoro, chloro, bromo or iodo, usually regarding halo substitution for a hydrogen atom in an organic compound.

"Haloalkyl" refers to an "alkyl" group in which one to four, especially one of its hydrogen atoms, is substituted by a "halogen" group.

"Haloaryl" refers to an "aryl" group substituted with from one to four halogen groups.

"Optional" or "optionally" means that the subsequently described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and phenyl wherein there is substitution.

The compounds of the present invention are generally named according to the IUPAC or Chemical Abstracts Service nomenclature system. The substituents on the ring system are as depicted above in the Summary of the Invention. For example, when the group attached at the 17a-carbon atom of the steroid is acyloxy, i.e. —O—(C=O)—$R^2$, and $R^2$ is ethyl, the compound of formula I is named 17$_a\beta$-hydroxy-7$\alpha$-methyl-D-homo-19-norandrost-4,16-dien-3-one propionate, or 7$\alpha$-methyl-17$_a\beta$-propionyloxy-D-homo-19-norandrost-4,16-dien-3-one, and is shown below:

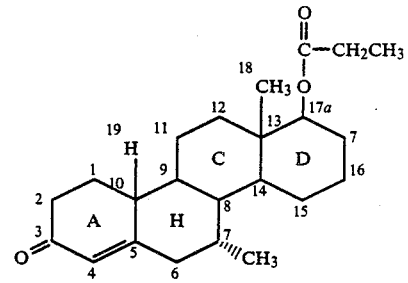

The five or six membered rings of the steroid molecule are often designated A, B, C and D as is shown immediately above.

Preferred compounds of the present invention are those compounds of formula I wherein $R^2$ is an alkyl, alkenyl, alkynyl, cycloalkyl, cycloalkylalkylene, aryl, or an arylalkylene. A more preferred subgroup includes those compounds when $R^2$ is an alkyl, alkenyl, alkynyl, cycloalkyl or cycloalkylene group. Yet more preferred subgroups include those compounds of formula I wherein $R^2$ is alkyl, particularly normal (or straight chain) alkyl, where $R^2$ contains from 1 to 16 carbon atoms. Especially preferred compounds are those where $R^2$ is ethyl, n-hexyl, n-nonyl, or n-tridecyl.

Additional preferred compounds are those where $R^2$ is aryl, particularly phenyl or arylalkylene, particularly 2-phenylethylene.

Process for Preparation

Reaction Sequences 1, 2 and 3 shown below may be used to prepare compounds of formula I.

In the Reaction Sequences the first structure and the last structure of each sequence will show the (CH₃—) for the 18-methyl group and (H—) for the 19-nor group. The intermediate structures may not show these groups in an attempt to depict a less complex reaction sequence.

Also, in Reaction Sequence 2 and 3 in certain steroid structures, a dotted line is shown connecting carbon atoms C(10), C(5) and C(6). This dotted line indicates for these intermediates that the exact location of a double bond is not known with certainty or that a mixture of the C(10)-C(5) and C(5)-C(6) unsaturated compounds is present. Regardless of the position of these double bonds, the C(4)-C(5) double bond is introduced with certainty at the end of Reaction Sequences 2 and 3.

atmosphere for about 12 to 36 hrs. The solvent is removed and the product, in most instances, may be used without further purification.

Compound 4 is prepared, according to Step C, by treating Compound 3 with a reducing agent, such as lithium aluminum hydride, in an appropriate solvent, such as diethyl ether and/or tetrahydrofuran. Compound 4 is obtained after treatment with sodium hydroxide solution, filtration and removal of solvent.

Compound 5 is obtained, according to Step D, by treating Compound 4 with an organic acid, such as acetic acid, and sodium or potassium nitrite at about −10° to +10° C. for about 1 to 24 hrs. After solvent removal and partitioning between ether/water, the ether layer is washed with water, sodium bicarbonate solution, dried and evaporated. Compound 5 is obtained in good yield.

Compound 6 is obtained, according to Step E, by treating Compound 5 with any agents which are useful

REACTION SEQUENCE 1

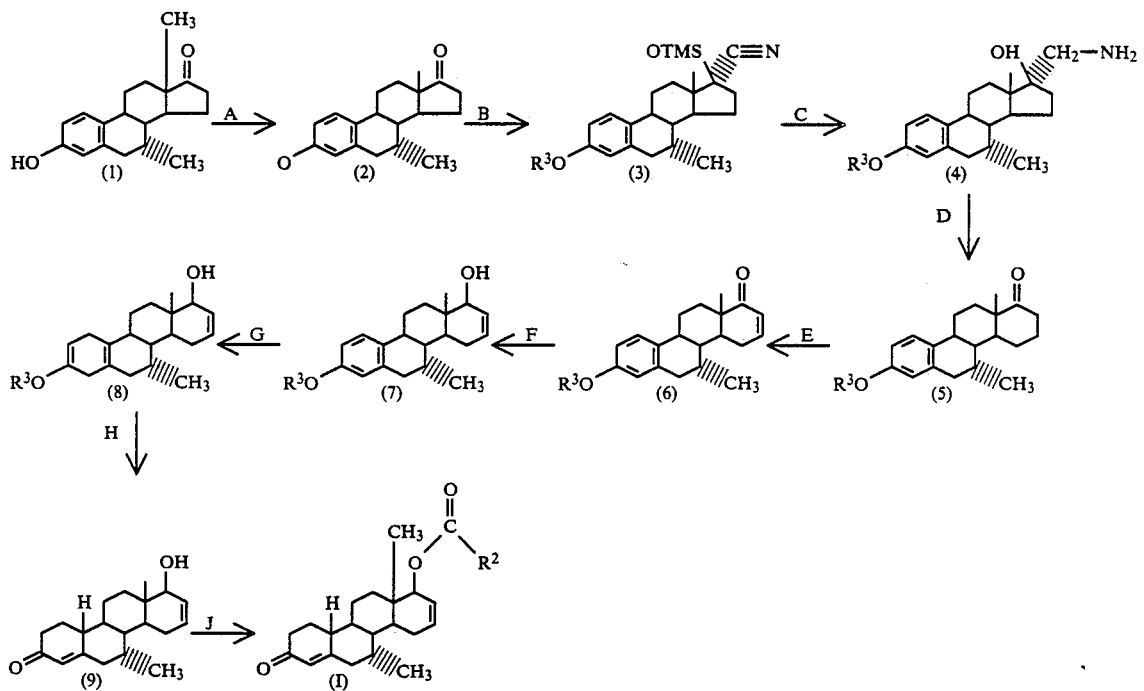

Reaction Sequence 1

The compounds of formula I are prepared, according to Step A, starting with 7α-methylestrone, Compound 1, and alkylating (e.g., methylating) the hydroxyl group at the 3-position of the A ring to produce the corresponding ether, Compound 2. $R^3$ of Reaction Sequence 1 is usually lower alkyl of one to six carbon atoms and alkyl as is described herein. This conversion may be accomplished by a number of methods, including the use of diazomethane or potassium carbonate-alkyl, i.e., $R^3$ (e.g. methyl) iodide in an aprotic solvent, such as acetone. The reaction mixture is normally stirred at ambient temperature for about 48 to 96 hr, followed by refluxing for about 12 to 24 hrs. Compound 2 is recovered by removal of the solvent.

Compound 3 is obtained, according to Step B, by treating Compound 2 with trimethylsilyl cyanide and zinc iodide at about ambient temperature in an inert to introduce a carbon-carbon double bond which is also conjugated with a ketone carbonyl group. These methods include treatment of Compound 5 with phenylselenenyl chloride at or about ambient temperature followed by treatment with hydrogen peroxide at ambient temperature. The solution is washed with water, saturated bicarbonate solution, water and dried. After chromatographic purification (usually preparative high pressure liquid chromatography, HPLC), Compound 6 is obtained.

Compound 7 is obtained, according to Step F, by treatment of Compound 6 with a reducing agent such as lithium aluminum hydride in an appropriate solvent. After careful treatment with water, a granular precipitate is obtained and removed by filtration. After the solution is washed, dried, and evaporated to dryness, Compound 7 is usually obtained in essentially a quantitative yield.

Compound 8 is obtained, according to Step G, by treatment of Compound 7 with a strong reducing agent, such as lithium in liquid ammonia. The crude solution is partitioned between ether and water, and the ether layer is washed, dried and evaporated to dryness. The residue is used without further purification.

Compound 9 is obtained, according to Step H, by removal of the lower alkyl (or methyl) group at the 3-position of the A-ring of the steroid. This may be achieved by treatment with concentrated acid, such as hydrochloric acid, for about 0.5 to 25 hr at about $-10°$ to 50° C. and neutralized. The aqueous solution is extracted with diethyl ether, and the ether portions are washed with water and evaporated to dryness. The residue is purified using preparative HPLC.

Compounds of the formula I are obtained, according to Step J, by treating Compound 9 with the acyl anhydride, e.g., $R^2$—(C=O)—O—(C=O)—$R^2$, anhydride or mixed acyl anhydrides corresponding to the desired $R^2$ in the presence of an organic base, such as pyridine at about ambient temperature for about 0.5 to 25 hr. After neutralization and purification, the compound of formula I is obtained in good yield. Alternatively, an acyl halide, $R^2$—(C=O)—X, where X is halogen and $R^2$ is as is defined herein, may be substituted for the acyl anhydride in this reaction.

In summary, then the compounds of Formula I are prepared by:

(a) alkylating (or methylating) the 3-hydroxyl group of 7α-methylestrone;

(b) reacting the product of step (a) with a trialkyl or arylsilyl cyanide to add across the 17-keto group;

(c) reducing the product of step (b) with a reducing agent to produce the 17-hydroxy-17-methylamine derivative;

(d) reacting the amine with nitrite to expand ring D of the steroid molecule;

(e) reacting the product of step (e) with phenylselenenyl chloride and hydrogen peroxide;

(f) reducing the product of step (e);

(g) reacting the product of step (f) with a strong reducing agent to partially reduce the aromatic ring A;

(h) reacting the product of step (g) with acid to dealkylate the 3-alkoxy group to produce the compound of formula I where $R^1$ is hydrogen; and (i) subsequently reacting the product of step (h) with an acyl anhydride or acyl halide to produce the compound of formula I where $R^1$ is —(C=O)—$R^2$, and $R^2$ is as defined herein.

Reactions describing the conversion of steroid compounds to numerous derivatives have been described by C. Djerassi (ed.) in *Steroid Reactions: An Outline for the Organic Chemist*, published by Holden-Day Publishing Company, Inc. of Belmont, Calif. in 1964 and J. Fried and J. Edwards, *Organic Reactions In Steroid Chemistry*, Vols. I and II, von Nostrand Reinhold Co., New York, N.Y., (1973), which are incorporated herein by reference.

The starting material and reagents used in this invention are readily available or may be prepared by methods known in the art, see, for example *Chemical Sources*, published by Directories Publishing Company, Inc., Flemington, N.J. in 1979 or *Organic Chemical Reagents* by L. Fieser and M. Fieser, published by John Wiley and Sons, Inc. of New York, N.Y. in 1967.

Reaction Sequence 2

Reaction Sequence 2 describes an alternative procedure to obtain the compounds of formula I.

REACTION SEQUENCE 2

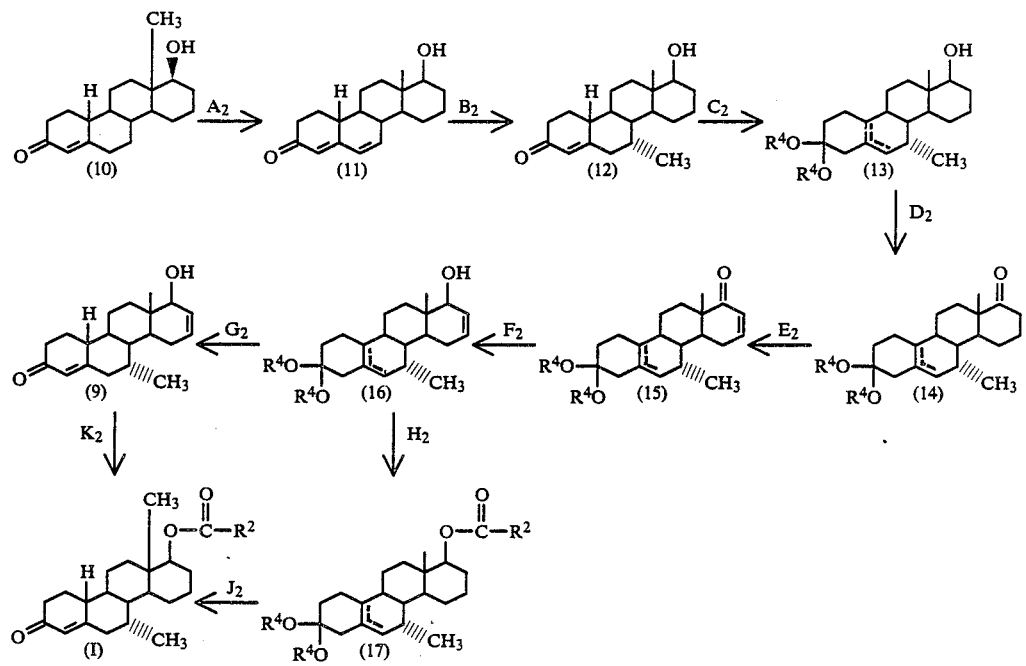

Compound 10 is prepared synthetically, as reported by J. Gutzwiller et al., *Helv. Chim. Acta.*, Vol. 61, pp 2397 ff (1978) which is incorporated herein by reference. Compound 10 is converted, according to Step $A_2$, to the 4,6-diene derivative, Compound 11, by treatment first with bromine followed by treatment with a mixture of lithium bromide and lithium carbonate. The reaction is conducted at about 0° to 80° C. for about 1 to about 10 hr. Compound 11 is obtained by filtration and removal of the solvent.

In Step $B_2$, Compound 12 is obtained by dissolving Compound 11 is an inert solvent and treatment with lithium dimethyl copper at about −10° to 100° C. for about 0.5 to 25 hr. The 7α-methyl derivative 12 is obtained upon purification and removal of the solvent.

Compound 13 is obtained, according to Step $C_2$, by treatment of Compound 12 with lower alcohol, $R^4OH$, where $R^4$ is lower alkyl containing 1 to 6 carbon atoms (e.g. methanol in Reaction Sequence 2), in the presence of a small amount of acid, such as sulfuric acid or p-toluenesulfonic acid. Compound 13 is obtained after washing with water, bicarbonate, and brine, drying and evaporation of the solvent.

Compound 14 is obtained, according to Step $D_2$, by dissolving Compound 13 in an inert solvent, such as methylene dichloride, and treatment with chromic oxide for about 1 to 10 hr at about −10° to 100° C. Compound 14 is obtained after washing with water, bicarbonate and brine, drying and evaporation of the solvent.

Compound 15, according to Step $E_2$, is obtained by treating Compound 14 with phenylselenenyl chloride in ethyl acetate followed by reaction with hydrogen peroxide in tetrahydrofuran (See the preparation and purification of Compound 6 in Reaction Sequence 1 above).

Compound 16, according to Step $F_2$, is obtained by reducing Compound 15 using lithium aluminum hydride in dry tetrahydrofuran. After purification as described for Step D in Reaction Sequence 1, Compound 16 is obtained in essentially quantitative yield.

Compound I may be obtained from Compound 16 by two different routes. The first route combines Steps $G_2$ and $K_2$. These steps are performed in essentially the same manner as Steps H and J in Reaction Sequence 1 with the same result. Compound I may also be obtained, according to Steps $H_2$ and $J_2$, by treatment with acyl anhydride as is described for Step J in Reaction Sequence 1, followed by mild treatment with water and acid as is also described in Step H in Reaction Sequence 1.

In summary, then, the compounds of formula I are prepared by:

(a) brominating D-homotestosterone followed by dehalogenation to produce the 4,6-diene;

(b) reacting the product of step (a) with lithium dimethyl copper to produce the 4-ene-7α-methyl derivative;

(c) reacting the product of step (b) with an alcohol and acid to produce the 3,3-dialkoxy derivative;

(d) oxidizing selectively the product of step (c) to produce the $17_a$-keto derivative;

(e) oxidizing the product of step (d) using phenylselenenyl chloride followed by hydrogen peroxide to produce the 4,16-diene-derivative;

(f) reducing the product of step (e) to produce the $17_a\beta$-hydroxy derivative;

(g) hydrolyzing the product of step (f) with acid to produce the 3-keto derivative, which is the compound of formula I where $R^1$ is hydrogen; and (h) reacting the product of step (g) with acyl anhydride or acyl halide to produce the compound of formula I where $R^1$ is acyl of the formula —(C=O)—$R^2$ and $R^2$ is as described herein.

A variation of this reaction sequence is delete steps (g) and (h) above and replace them with the following steps:

(i) reacting the product of step (f) with acyl anhydride or acyl halide to produce the 3,3-dialkoxy derivative and (j) hydrolyzing the product of step (i) with acid to produce the compound of formula I, where $R^1$ is acyl of the formula —(C=O)—$R^2$ and $R^2$ is as defined herein.

Optionally, the product of step (g) may be further hydrolyzed using water, heat and mild acid to produce the $17_a\beta$-hydroxy derivative, which is the compound of formula I where $R^1$ is hydrogen.

Reaction Sequence 3

Reaction Sequence 3 describes an additional alternative procedure to obtain the compounds of formula I.

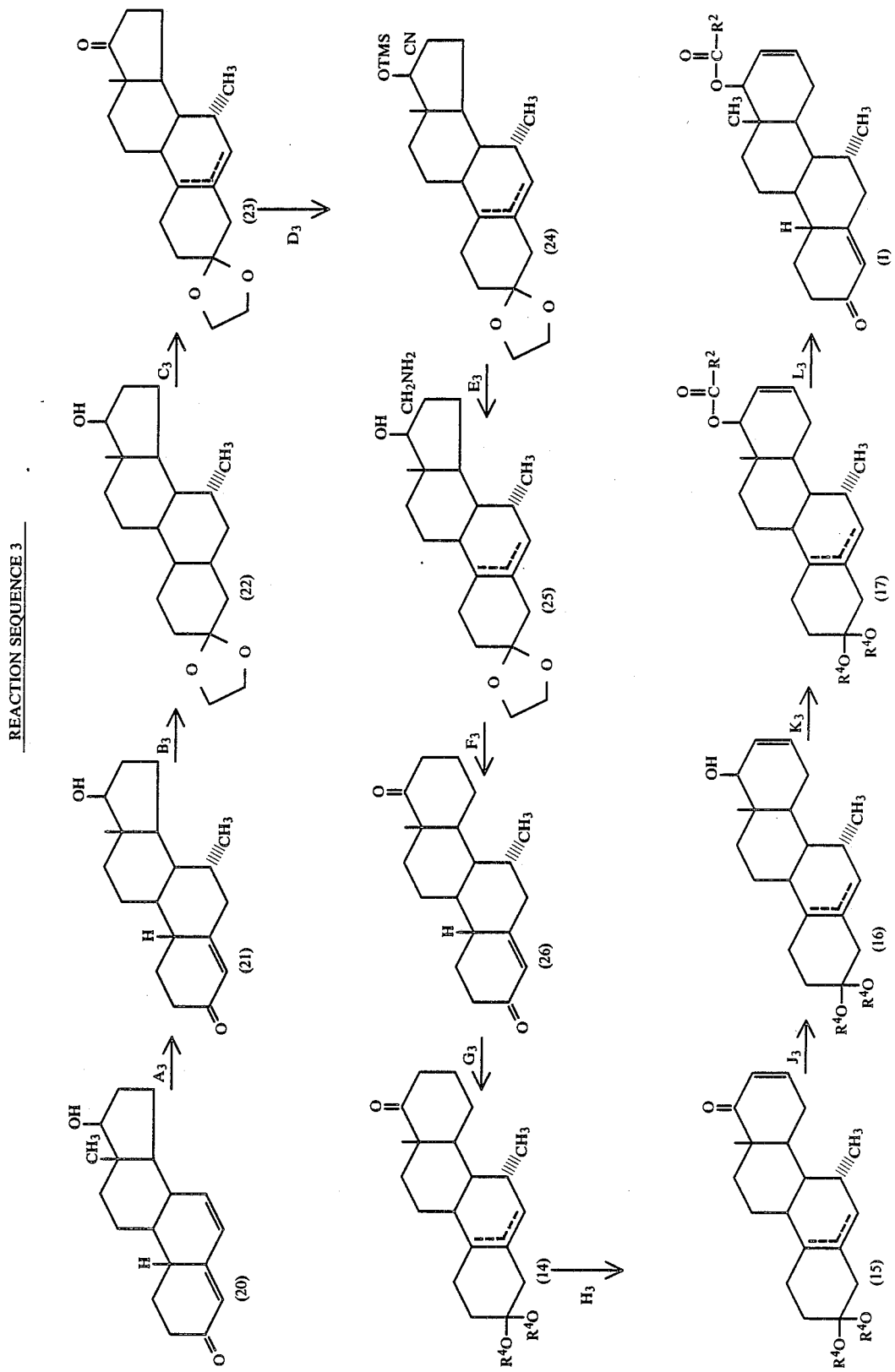

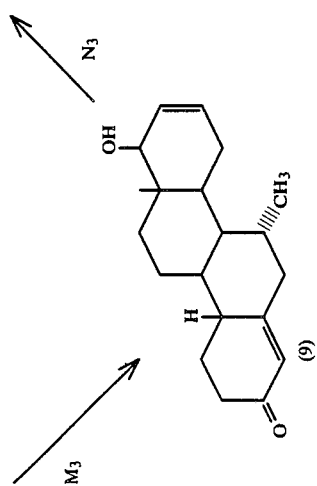

Starting with Compound 20 which is available according to the methods described by J. A. Zedric et al., *Steroids*, Vol. 1, p 233 (1963). In Step A$_3$, Compound 20 is converted to the 7α-methyl derivative, Compound 21, using lithium dimethyl copper. The reaction is performed in an inert solvent for about 1 to 25 hr. at about −10° to 100° C. After purification involving washing with water, bicarbonate and brine, drying and removal of the solvent, Compound 21 is obtained in good yield.

Compound 22 is obtained, according to Step B$_3$, by reaction with Compound 21 with ethylene glycol and acid, such as sulfuric acid or p-toluenesulfonic acid. After purification by washing with water, bicarbonate, and brine, drying and evaporation of the solvent, Compound 22 is obtained in good yield.

Compound 23 is obtained, according to Step C$_3$, by treatment of Compound 22 with chromic oxide in methylene chloride. The reaction is performed at about −10° to +45° C. for about 1 to 25 hrs. Compound 23 is obtained after washing with water, bicarbonate and brine, drying and evaporation of the solvent.

Compound 24 is obtained, according to Step D$_3$, by treatment of the 17-keto derivative, Compound 23, with trimethylsilyl cyanide and zinc iodide in methylene chloride. After work up as is described above for Step B in Reaction Sequence 1, Compound 24 may be used without further purification.

Compound 25 is obtained, according to Step E$_3$, by reducing using lithium hydride in tetrahydrofuran-diethyl ether, and purified as is described for Step C of Reaction Sequence 1.

Compound 26 is obtained, according to Step F$_3$, by oxidizing the 17-hydroxy derivative, Compound 25, using acetic acid and nitrite ion, followed by purification, in a manner similar to that described above for Step D of Reaction Sequence 1.

Compound 14 is obtained, according to Step G$_3$, by treatment Compound 26 with methanol and acid such as sulfuric acid or p-toluenesulfonic acid. Compound 14 is purified by successive washing with water, sodium bicarbonate, and brine solution, drying and evaporating the solvent.

Compound I is subsequently obtained by performing Steps H$_3$, J$_3$, K$_3$ and L$_3$, in the same manner as is described for Steps E$_2$, F$_2$, H$_2$ and J$_2$, respectively, in Reaction Sequence 2.

Alternatively, Compound I is also obtained by performing Steps H$_3$, J$_3$, M$_3$ and N$_3$ in the same manner as is described for Steps E$_2$, F$_2$, H$_2$ and J$_2$, respectively, in Reaction Sequence 2.

In summary then, the compounds, of formula I are prepared by:

(a) reacting 6-ene testosterone with lithium dimethyl copper to produce the 7α-methyl-derivative;

(b) reacting the product of step (a) with ethylene glycol to produce the 1,3-dioxolane derivative at the 3-position of the steroid;

(c) oxidizing the product of step (b) with chromic oxide to produce the 17-keto derivative;

(d) reacting the product of step (c) with trimethylsilyl cyanide in the presence of zinc iodide to produce the corresponding 17-ether-17-nitrile;

(e) reducing of the nitrile of step (d) to produce the 17-ether-17-methyleneamine derivative;

(f) reacting the product of step (e) with nitrite to produce the D-homo-17$_a$-keto derivative;

(g) reacting the product of step (f) with alcohol and acid to form the 3,3-dialkoxy derivative;

(h) reacting the product of step (g) with phenylselenenyl chloride and hydrogen peroxide to produce the 16-ene derivative;

(i) reducing the product of step (h), the 17$_a$-keto derivative, to the 17$_a$β-hydroxy derivative;

(j) reacting the product of step (i) with acyl anhydride or acyl halide to produce the 3,3-dialkoxy-17$_a$β ester; and (k) hydrolyzing the product of step (j) in the presence of mild acid to produce the compound of formula I, where R$^1$ is acyl as is defined herein.

Optionally, the ester of step (k) may be subsequently hydrolyzed with acid and water to produce the compound of formula I, where R$^1$ is hydrogen.

A variation of this process substitutes the following steps for substeps (j) and (k) above:

(l) hydrolyzing the product of step (i) in the presence of acid to produce the compound of formula I where R$^1$ is hydrogen; and optionally (m) reacting the 17$_a$β-hydroxy product of step (l) with acyl anhydride or acyl halide to produce the compound of formula I, where R$^1$ is acyl and R$^2$ is as defined herein.

Use of the Compounds

Another embodiment of the present invention involves a method useful in the control of male fertility in a mammal, particularly a human being, which method comprises administering to a subject in need of such treatment a therapeutically effective amount of the compound of formula I. A preferred method includes oral administration of the compound of formula I, particularly where R$^2$ is ethyl. The compounds can also be used in other oral androgen therapies known in the art.

The compounds of the invention may be administered alone or in combination with other pharmaceutical agents. In one preferred therapy the compounds of this invention are used in combination with LHRH antagonists. In this therapy the compounds of the invention function as potent oral androgens and maintain male libido without liver toxicity. LHRH antagonists are attractive male contraceptive agents which have the side effect of decreasing male libido. Representative LHRH antagonists are described in the literature. See, for example, the book *LHRH and Its Analogs, Contraceptive and Therapeutic Applications*, B. H. Vickery et al, eds, MTP Press Limited, Lancaster, PA, 1984 ("Vickery et al").

As pointed out by M. V. Nekola et al in chapter 10 of the Vickery et al text, LHRH antagonists have been synthesized having substitution in one or more of the 1, 2, 4, 6, and 10 positions. U.S. Pat. No. 4,341,767 of Nestor et al shows LHRH antagonists having the LHRH structure substituted at the 1, 2, 3 and/or 6 positions with a glycinamide or a —NH—R′ (wherein R′ is an alkyl or the like) at the 10 position; U.S. Pat. No. 4,431,635 of Coy et al shows LHRH antagonists having variable amino acid residues at the 1, 2, and 6 positions and optionally at the 3 and 10 positions. *J Med Chem* (1974) 17, 9: 101, by Rees et al, shows a variety of 2-modified analogs of LHRH and their antagonist activity. These materials are incorporated herein by reference.

When used in combination with LHRH antagonists the LHRH antagonist dose level is from about 0.005% to about 20 mg/kg/day as is known in the art.

A preferred composition includes compositions comprising compounds of formula I for oral administration to a human being, particularly where $R^1$ is hydroxyl, and also where $R^1$ is acyl and $R^2$ is ethyl.

Utility and Administration

The compounds of this invention have been shown to be effective in animal models for antigonado-tropic effect and, in the control of spermatogenesis in male mammals. These compounds are in large doses, useful in male contraception, in a mammal, particularly a human being, while maintaining the male libido. In smaller doses, a paradoxical result is observed in that these compounds increase spermatogenesis, while maintaining male libido.

For instance, the compound of formula I where $R^1$ is ethyl, when tested in rats, was found to have 40 times the androgenic activity of testosterone via subcutaneous injection and 6 times the activity of 17α-methyltestosterone when orally administered. Further, the androgenic effect of this compound when orally administered was 6 times the effect for methyl testosterone.

Although not completely understood at this time, the compounds of this invention exhibit potent antigonadoptropic-androgenic activity in the same compound when orally administered. These compounds appear to have antigonadoptropic activity which interferes with spermatogenesis at the testicular level by supressing testosterone synthesis via feedback control and also have androgenic activity to maintain libido and secondary sex characteristics.

Administration of the active compounds and salts described herein can be via any of the accepted modes of administration for therapeutic agents. These methods include oral, rectal, parenteral, transdermal, subcutaneous and other system modes. The preferred method of administration is oral, except in those cases where the subject is unable to ingest, by himself, any medication. In those instances it may be necessary to administer the composition parenterally.

Depending on the intended mode, the compositions may be in the form of solid, semi-solid or liquid dosage forms, such as, for example, tablets, suppositories, pills, capsules, powders, liquids, suspensions, or the like, preferably in unit dosage forms suitable for single administration of precise dosages. The compositions will include a conventional pharmaceutical excipient and an active compound of formula I or the pharmaceutically acceptable salts thereof and, in addition, may include other medicinal agents, pharmaceutical agents, carriers, adjuvants, diluents, etc.

The amount of active compound administered will, of course, be dependent on the subject being treated, the subject's weight, the severity of the affliction, the manner of administration and the judgement of the prescribing physician. However, an effective dosage for reduction of spermatogenesis is in the range of about 1–10 mg/kg/day, preferably about 6 mg/kg/day. For an average 70 kg human, this would amount to about 70–700 mg/day, or preferably about 420 mg/day.

An effective dosage for increasing spermatogenesis is in the range of about 0.01 to 0.99 mg/kg/day, preferably about 0.5 mg/kg/day. For an average 70 kg human this would amount to about 0.7 to 69 mg/day, preferably about 35/mg/day.

In oral androgen therapy regimens, doses of from about 0.02 to about 1 mg/kg/day and especially from about 0.03 to about 0.80 mg/kg/day are useful for male androgen replacement and doses from about 0.04 to about 5 mg/kg/day and especially 0.05 to about 4 mg/kg/day are useful for female breast carcinoma treatment. Such levels are effective androgenic response levels. These levels are also to be used in combination products with LHRH antagonists.

For solid compositions, conventional nontoxic solids include, for example, pharmaceutical grades of mannitol, lactose, starch, magnesium stearate, sodium saccharin, talc, cellulose, glucose, sucrose, magnesium carbonate, and the like may be used. The active compound as defined above may be formulated as suppositories using, for example, polyalkylene glycols, for example, propylene glycol, as the carrier. Liquid pharmaceutically administerable compositions can, for example, be prepared by dissolving, dispersing, etc. an active compound as defined above and optional pharmaceutical adjuvants in a excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 15th Edition, 1975. The composition or formulation to be administered will, in any event, contain a quantitiy of the active compound(s), a therapeutically effective amount, i.e. in an amount effective to achieve the desired fertility control in the subject being treated.

For oral administration, a pharmaceutically acceptable non-toxic composition is formed by the incorporation of any of the normally employed excipients described above. Such compositions take the form of solutions, suspensions, tablets, pills, capsules, powders, sustained release formulations and the like. Such compositions may contain 1%–95% active ingredient, preferably 1–70%.

Parenteral administration, if used, is generally characterized by injection, either subcutaneously, intramuscularly or intravenouously. Injectables can be prepared in conventional forms, either as liquid solutions or suspensions, solid forms suitable for solution or suspension in liquid prior to injection, or as emulsions. Suitable excipients are, for example water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently revised approach for parenteral administration employs the implantation of a slow-release or sustained-release system, such that a constant level of dosage is maintained. See, e.g., U.S. Pat. No. 3,710,795, which is incorporated herein by reference.

The following examples serve to illustrate the invention. They should not be construed as narrowing it, or limiting its scope. The Steps A, B, C, etc. cited in the Examples refer to the corresponding Steps in Reaction Sequence 1.

EXAMPLE 1

7α-Methyl Estrone Methyl Ether (Step A to Produce Compound 2)

A slurry of 14.94 g of 7α-methyl estrone (Compound 1, prepared according to J. Kalvoda et al., *Helv. Chim Acta.* Vol. 50, pp. 281–288 (1967)) and 28 g of anhydrous potassium carbonate in 600 ml of acetone and 100 ml of methyl iodide is stirred under argon at ambient temperature and pressure for 3 days. Thin layer chromatographic analysis indicates the reaction is about 90% complete. The mixture is then heated to a slow reflux (oil bath temperature, 70° C.) and is refluxed for 24 hr, at which time the reaction is complete. The solvent is removed under reduced pressure and the residue is dissolved in methylene chloride (500 ml) and water (200 ml). The layers are separated and the aqueous layer is washed twice with 150 ml portions of methylene chloride. The combined methylene chloride extracts are combined and washed twice with 200 ml portions of water, dried using sulfate, and evaporated to dryness using reduced pressure. There is obtained 14.8 g (about 100% yield) of 4-methoxy 7α-methylestrone which has the following spectral properties:

Proton magnetic resonance spectrum (in CDCl$_3$): 0.88 (d, Y=6 Hz, C$_7$CH$_3$); 0.91 (C$_{18}$CH$_3$); 3.76 (OCH$_3$); 6.60 (C$_4$H); 6.72 (dd, Y=9 Hz, Y=3 Hz, C$_2$H); 7.21δ (d, Y=9 Hz, C$_1$H).

EXAMPLE 2

17-Cyano-3-methoxy-7α-methyl-17-trimethylsilyloxyestra-1,3,5(10)-triene (Step B to produce Compound 3)

A mixture of 10.74 g of Compound 2 (from Example 1), 10 ml of chloroform, 14 ml of trimethylsilyl cyanide, and 40 mg of zinc iodide is stirred at ambient temperature and pressure under argon for 19 hr. The solvent and excess reagent are removed using reduced pressure, and the residue is dissolved in a mixture of ether (300 ml) and water (100 ml). The layers are separated and the aqueous layer is extracted twice with ether (150 ml). The combined ether extracts are washed twice with water (100 ml), dried over sodium sulfate and evaporated to dryness using reduced pressure. An essentially quantitative yield (14.45 g) of Compound 3 is obtained which is used in Example 3 without further purification. The structure of Compound 3 is confirmed by the following spectral data:

Infrared spectrum: $\lambda_{max}^{film}$: 4.5 (C≡N); 6.20 & 6.40μ (aromatic).

Proton magnetic resonance spectrum (in CCl$_4$): 0.22 (OTMS); 0.81 (C$_{18}$CH$_3$); 0.92 (d, Y=7 Hz, C$_7$CH$_3$); 3.73 (OCH$_3$); 6.52 (C$_4$H); 6.52 (dd, Y=9 Hz, Y=3 Hz; C$_2$H); 7.13δ (d, Y=9 Hz), C$_1$H).

EXAMPLE 3

17-Hydroxy-3-methyl-7α-methyl-17-aminomethylestra-1,3,5(10)-triene (Step C to produce Compound 4)

To a slurry of lithium aluminum hydride, 50 ml of anhydrous diethyl ether, and 50 ml of anhydrous tetrahydrofuran (which is dried by distillation from methylmagnesium bromide and storage over molecular sieves) is added, under argon, a solution of 14.45 g of Compound 3 (from Example 2) in 50 ml of dry tetrahydrofuran. The reaction mixture is cooled during addition in an ice-water bath. After the solution containing Compound 3 is added, the ice bath is removed, and the reaction mixture is stirred at ambient temperature for 3 hr. To the reaction mixture, 4.5 ml of water is added dropwise with vigorous stirring, followed by 4.5 ml of 15% sodium hydroxide solution. Upon further stirring, a white granular precipitate is formed. The solution is filtered, and the precipitate is washed with several 50 ml portions of diethyl ether. The combined ether solutions are dried over sodium sulfate and evaporated to dryness at reduced pressure to produce 10.8 g (about 91% yield) of a crystalline product which was used in the the following example without further purification. The structure of Compound 4 is confirmed by the following spectral data:

Infrared spectrum: $\lambda_{max}^{nujol}$: 3.05, 3.15 & 3.25 (OH, NH$_2$); 6.20 & 6.35μ (aromatic).

Proton magnetic resonance spectrum (in CCl$_4$, CD$_3$OD; 1:1): 0.80 (d, Y=7 Hz, C$_7$CH$_3$); 0.88 (C$_{18}$CH$_3$); 3.70 (OCH$_3$); 6.53 (C$_4$H); 6.60 (dd, Y=8 Hz, Y=2 Hz, C$_2$H); 7.14δ (d, Y=8 Hz, C$_1$H).

EXAMPLE 4

17$_a$-Keto-3-methoxy-7α-methyl-D-homoestra-1,3,5(10)-triene (Step D to produce Compound 5)

To a solution of 10.8 g of Compound 4 in 300 ml of glacial acetic acid and 50 ml of water is added, dropwise over 30 min, a solution of 5.9 g of sodium nitrite in 50 ml of water, while the reaction mixture is cooled in an ice-water bath. After stirring for 2 hr at ice-water temperature, the mixture is warmed to ambient temperature and stirred for 18 hr. The reaction mixture is cooled to ice-water temperature and an additional 5.9 g of sodium nitrite is added with vigorous stirring. The mixture is stirred for 1 hr at ice-water temperature followed by stirring at ambient temperature for 4 hr. The solvent is evaporated below ambient temperature using a lyophizer, and the residue is dissolved in 500 ml of diethyl ether and 200 ml of water. The layers are separated, and the aqueous layer is extracted with two 150 ml portions of diethyl ether. The combined ether extracts are washed twice with 250 ml of water, twice with 250 ml of saturated sodium bicarbonate solution, once with 250 ml of water, dried over sodium sulfate and evaporated to dryness using reduced pressure.

The 20 g of yellow solid obtained is chromatographed using a Waters 500 preparation high pressure liquid chromatograph (HPLC) using a normal phase silica gel cartridge with elution using 5% ethyl acetate/petroleum ether (bp 31°–60° C.). 4.51 G of pure Compound 5 is obtained (55% yield) having the following analytical and spectral data:

Infrared spectrum: $\lambda_{max}^{nujol}$: 5.85 (C=O); 6.20 & 6.35μ (aromatic).

Proton magnetic resonance spectrum (in CDCl$_3$): 0.80 (d, Y=7 Hz, C$_7$CH$_3$); 1.08 (C$_{18}$CH$_3$); 3.79 (OCH$_3$); 6.53 (C$_4$H); 6.65 (dd, Y=8 Hz, Y=2 Hz, C$_2$H); 7.18δ (d, Y=8 Hz).

High resolution mass spectrum: Calcd. for C$_{21}$H$_{28}$O$_2$: 312.2089; Found: 312.2075.

EXAMPLE 5

17$_a$-Keto-3-methoxy-7α-methyl-D-homoestra-1,3,5(10),16-tetraene (Step E to produce Compound 6)

To a solution of 5.68 g of Compound 5 (from Example 4) in 130 ml of ethyl acetate is added, under argon, 4.38 g of phenylselenenyl chloride. After stirring at ambient temperature for 3 hr, 1.44 g of additional phenylselenenyl chloride is added with continued stirring for an additional hr. Water (45 ml) is added, and the mixture is vigorously stirred for 5 min and transferred to a separatory funnel. The aqueous layer is removed, and the ethyl acetate layer is washed three times with 30 ml of water. The ethyl acetate layer is returned to the reaction flask and diluted with 45 ml of tetrahydrofuran. This mixture is cooled using an ice-water bath and 4.1 ml of 30% aqueous hydrogen peroxide is added. The mixture is stirred at ambient temperature for 1 hr and diluted to a volume of approximately 300 ml with diethyl ether. The solution is washed twice with 100 ml of water, twice with 100 ml of saturated sodium bicarbonate solution and once with 100 ml of water, dried using sodium sulfate and evaporated to dryness using reduced pressure. The residue (6.67 g) is chromatographed using a Waters 500 preparative high pressure liquid chromatograph (HPLC) using a normal-phase silica gel cartridge. Elution from the column occurs using 6% ethyl acetate-petroleum ether (bp 35°–60° C.) and produces 3.1 g of Compound 6 (55% yield). The following analytical and spectral data agree with the proposed structure:

Infrared spectrum: $\lambda_{max}^{nujol}$: 5.95 (=C—C=O); 6.20 & 6.35 (aromatic).

Proton magnetic resonance spectrum (in CDCl$_3$): 0.80 (d, Y=7 Hz, C$_7$CH$_3$); 1.02 (C$_{18}$CH$_3$); 3.77 (OCH$_3$); 5.90 (dd, Y=9 Hz, Y=2 Hz, C$_{17}$H); 6.60 (C$_4$H); 6.72 (dd, Y=8 Hz, Y=2 Hz); 6.8 (m, C$_{16}$H); 7.20δ (C$_1$H).

EXAMPLE 6

17$_a$β-Hydroxy-3-methoxy-7α-methyl-D-homoestra-1,3,5(10),16-tetraene (Step F to produce Compound 7)

Compound 6 (from Example 5), 3.79 g, is dissolved in 50 ml of anhydrous diethyl ether and 100 ml of dry tetrahydrofuran (dried by distillation from methylmagnesium bromide and stored over molecular sieves). Under a blanket of argon, the mixture is cooled to about 0° C. using an ice-water bath, and 589 mg of lithium aluminum hydride is added in small portions to keep foaming under control. The solution is stirred at ice-water temperature for 45 min and 10 ml of water is added dropwise with vigorous stirring until a white granular precipitate has formed. The precipitate is filtered off and washed three times with 50 ml of diethyl ether. The filtrate is combined with the washings, and the combined solution is dried using anhydrous sodium sulfate, filtered and evaporated to dryness using reduced pressure. Compound 7 (3.85 g, 100% yield) is used in the next step without further purification. The structure of Compound 7 is confirmed by the following spectral data:

Infrared spectrum $\lambda_{max}^{nujol}$: 2.9 (OH); 6.20 & 6.35μ (aromatic).

Proton magnetic resonance spectrum (in CDCl$_3$): 0.80 (d, Y=7 Hz, C$_7$CH$_3$); 0.85 (C$_{18}$CH$_3$); 3.77 (OCH$_3$); 5.57 (d, Y=7 Hz, C$_{17}$H); 5.72 (dm, C$_{16}$H); 6.57 (C$_4$H); 6.63 (dd, Y=8 Hz, C$_2$H); 7.19δ (d, Y=8 Hz, C$_1$H).

EXAMPLE 7

17$_a$β-Hydroxy-3-methoxy-7α-methyl-D-homostra-2,5(10),16-triene (Step G to produce Compound 8)

Liquid ammonia (20 ml) is condensed into a flame-dried reaction flask under argon at Dry Ice-acetone temperature. Small pieces of lithium wire, a total weight of 1.01 g, are dissolved in the ammonia. Compound 7, 3.85 g (from Example 6), is dissolved in 130 ml of dry tetrahydrofuran (dried by distillation from methylmagnesium bromide and stored over molecular sieves), added to the ammonia solution, and stirred for 45 min at Dry Ice-acetone temperature. A mixture of 22 ml of absolute ethanol and 33-ml of tetrahydrofuran is added dropwise over 15 min. The cooling bath is removed, and the still-blue solution is stirred. At this point, no more Dry Ice is added to the Dry Ice-condenser. The blue color disappears after 20 min, the ammonia is allowed to evaporate, and the residual solution is diluted with 300 ml of ether and 200 ml of water. The layers are separated, and the aqueous layer is extracted twice with 100 ml of diethyl ether. The combined ether solutions are washed twice with water dried over sodium sulfate and evaporated to dryness using reduced pressure. The crude residue of Compound 8 weighing 3.38 g is obtained and is used in the next step without further purification.

The following spectral data agree with the prosposed structure:

Infrared spectrum: $\lambda_{max}^{nujol}$: 3.1 (OH); 5.9 & 6.0μ (C=C).

Proton magnetic resonance spectrum (in CDCl$_3$): 0.74 (d, Y=8 Hz, C$_7$CH$_3$); 0.80 (C$_{18}$CH$_3$); 3.60 (OCH$_3$); 4.64 (C$_2$H); 5.47 (d, Y=7 Hz, C$_{17}$H); 5.68δ (dm, Y=7 Hz, C$_{16}$H).

EXAMPLE 8

17$_a$β-Hydroxy-7α-methyl-D-homo-19-norandrost-4,16-dien-3-one (Step H to produce Compound 9)

To a solution of 3.38 g of Compound 8 (from Example 7) in 50 ml of 80% aqueous methanol is added 1.25 ml of concentrated hydrochloric acid. The solution is stirred at reflux temperature for 20 min and cooled to ambient temperature. After neutralization using solid sodium acetate, the mixture is added to a saturated sodium chloride solution. The precipitate is extracted using three 250 ml portions of diethyl ether. The combined ether extracts are washed with 160 ml of water, dried using sodium sulfate, and evaporated to dryness using reduced pressure. The 4 g crude residue is chromatographed using a Waters 500 preparative HPLC instrument using a normal phase silica gel cartridge. Elution with 5% ethyl acetate/chloroform affords 2.22 g of pure Compound 9 (overall 58% yield, for Examples 6, 7 and 8). The structure of Compound 9 (which is the compound of formula I, where R$^1$ is hydrogen) is confirmed by the following spectral data:

Infrared spectrum: $\lambda_{max}^{film}$: 2.95 (OH); 6.0 & 6.25μ (=C—C=O).

Proton magnetic resonance spectrum (in CDCl$_3$): 0.80 (d, Y=7 Hz, C$_7$CH$_3$); 0.88 (C$_{18}$CH$_3$); 3.94 (b, $C_{17a}H$); 5.41 (d, Y=8 Hz, $C_{16}H$); 5.71 (dm, $C_{17}H$); 5.71 (dm, $C_{16}H$); 5.82 & ($C_4$—H).

EXAMPLE 9

7α-Methyl-17$_a$β-propionyloxy-D-homo-19-norandros-4,16dien-3-one (Step J to produce Compound I where $R^1$ is acyl and $R^2$ is ethyl)

(a) To a solution of 1.0 g of Compound 9 (from Step H) and 20 ml of dry pyridine (dried over potassium hydroxide pellets) is added 3 ml of propionic anhydride followed by stirring at ambient temperature for 42 hr. The mixture is added to 150 ml of a 3% hydrochloric acid solution, and the precipitate is extracted into three 80 ml portions of diethylether. The combined ether extracts are washed once with 100 ml of water, dried using anhydrous sodium sulfate, and evaporated to dryness using reduced pressure. A crystalline residue of 1.1 g of Compound I is obtained, which is recrystallized from ether-hexane to produce an analytical sample.

The structure of Compound I, where $R^1$ is acyl and $R^2$ is ethyl, is confirmed by the following spectral data:

Infrared spectrum: $\lambda_{max}^{nujol}$: 5.75 (O—C=O); 6.00 & 6.25μ (=C—C=O).

Proton magnetic resonance spectrum (in $CDCl_3$): 0.72 (d, $C_7CH_3$); 0.91 ($C_{18}CH_3$); 5.12 (b, $C_{17a}H$); 5.41 (d, Y=9 Hz, $C_{16}H$); 5.76 (dm, $C_{15}H$); 5.88δ ($C_4H$).

High-resolution mass spectrum: Calcd. for $C_{23}H_{32}O_3$: 356.2351; Found: 356.2323.

(b) Similarly, proceeding as in Subpart (a) above, but substituting a stoichiometrically equivalent amount of
acetic anhydride;
butanoic anhydride;
isobutanoic anhydride;
n-octanoic anhydride;
dodecanoic anhydride;
hexadecanoic anhydride;
eicosanoic anhydride;
tetracosanoic anhydride;
acrylic anhydride;
methacrylic anhydride;
3-methylacrylic anhydride;
2-octenoyl anhydride;
2-hexadecenoyl anhydride;
2-tetracosenoyl anhydride;
propynoic anhydride;
2-hexynoic anhydride;
2-hexadecynoyl anhydride;
2-tetracosynoyl anhydride;
2-chloroacetic anhydride;
3-bromopropionoyl anhydride;
2-chlorohexanoyl anhydride;
2-chlorohexadecanoyl anhydride;
2-chlorotetracosanoyl anhydride;
benzoyl anhydride;
4-chlorobenzoyl anhydride;
4-methylbenzoyl anhydride;
2-naphthoic anhydride;
4-chloro-2-naphthoyl anhydride;
6-bromo-2-naphthoyl anhydride;
phenylacetic anhydride;
3-phenylpropionic anhydride; or
6-phenylhexanoyl anhydride for propionic anhydride, the following esters of Compound 9 are obtained:
7α-methyl-17$_a$β-acetyloxy-D-homo-19-norandrost-4,16-dien-3-one;
7α-methyl-17$_a$β-butanoyloxy-D-homo-19-norandrost-4,16-dien-3-one;
7α-methyl-17$_a$β-isobutanoyloxy-D-homo-19-norandrost-4,16-dien-3-one;
7α-methyl-17$_a$β-n-octanoyloxy-D-homo-19-norandrost-4,16-dien-3-one;
7α-methyl-17$_a$β-dodecanoyloxy-D-homo-19-norandrost-4,16-dien-3-one;
7α-methyl-17$_a$β-hexadecanoyloxy-D-homo-19-norandrost-4,16-dien-3-one;
7α-methyl-17$_a$β-eicosanoyloxy-D-homo-19-norandrost-4,16-dien-3-one;
7α-methyl-17$_a$β-tetracosanoyloxy-D-homo-19-norandrost-4,16-dien-3-one;
7α-methyl-17$_a$β-acryloyloxy-D-homo-19-norandrost-4,16-dien-3-one;
7α-methyl-17$_a$β-methacryloyloxy-D-homo-19-norandrost-4,16-dien-3-one;
7α-methyl-17$_a$β-(3-methylacryloyloxy)-D-homo-19-norandrost-4,16-dien-3-one;
7α-methyl-17$_a$β-(2-octenoyloxy)-D-homo-19-norandrost-4,16-dien-3-one;
7α-methyl-17$_a$β-(2-hexadecenoyloxy)-D-homo-19-norandrost-4,16-dien-3-one;
7α-methyl-17$_a$β-(2-tetracosenoyloxy)-D-homo-19-norandrost-4,16-dien-3-one;
7α-methyl-17$_a$β-propynyloxy-D-homo-19-norandrost-4,16-dien-3-one;
7α-methyl-17$_a$β-(2-hexynyloxy)-D-homo-19-norandrost-4,16-dien-3-one;
7α-methyl-17$_a$β-(2-hexadecynyloxy)-D-homo-19-norandrost-4,16-dien-3-one;
7α-methyl-17$_a$β-(2-tetracosynyloxy)-D-homo-19-norandrost-4,16-dien-3-one;
7α-methyl-17$_a$β(2-chloroacetyloxy)-D-homo-19-norandrost-4,16-dien-3-one;
7α-methyl-17$_a$β-(3-bromopropionyloxy)-D-homo-19-norandrost-4,16-dien-3-one;
7α-methyl-17$_a$β-(2-chlorohexanoyloxy)-D-homo-19-norandrost-4,16-dien-3-one;
7α-methyl-17$_a$β-(2-chlorohexadecanoyloxy)-D-homo-19-norandrost-4,16-dien-3-one;
7α-methyl-17$_a$β-(2-chlorotetracosanoyloxy)-D-homo-19-norandrost-4,16-dien-3-one;
7α-methyl-17$_a$β-benzoyloxy-D-homo-19-norandrost-4,16-dien-3-one;
7α-methyl-17$_a$β-(4-chlorobenzoyloxy)-D-homo-19-norandrost-4,16-dien-3-one;
7α-methyl-17$_a$β-(4-methylbenzoyloxy)-D-homo-19-norandrost-4,16-dien-3-one;
7α-methyl-17$_a$β-(2-naphthoyloxy)-D-homo-19-norandrost-4,16-dien-3-one;
7α-methyl-17$_a$β-(4-chloro-2-naphthoyloxy)-D-homo-19-norandrost-4,16-dien-3-one;
7α-methyl-17$_a$β-(6-bromo-2-naphthoyloxy)-D-homo-19-norandrost-4,16-dien-3-one;
7α-methyl-17$_a$β-phenylacetyloxy-D-homo-19-norandrost-4,16-dien-3-one;
7α-methyl-17$_a$β-(3-phenylpropionoyloxy)-D-homo-19-norandrost-4,16-dien-3-one; or
7α-methyl-17$_a$β-(6-phenylhexanoyloxy)-D-homo-19-norandrost-4,16-dien-3-one.

(c) Similarily, proceeding as in Subpart (a) above but substituting a stoichiometrically equivalent amount of
acetyl chloride;
propionyl chloride;
n-octanoyl chloride;
eicosanoyl chloride;

acryloyl chloride;
methacryloyl chloride;
2-tetracosenoyl chloride;
propynoyl chloride;
2-tetracosynoyl chloride;
2-chloroacetyl chloride;
2-chlorotetracosanoyl chloride;
benzoyl chloride;
4-chlorobenzoyl chloride;
4-methylbenzoyl chloride;
2-naphthoyl chloride;
6-bromo-2-naphthoyl chloride;
phenylacetyl chloride;
3-phenylpropionyl chloride; or
6-phenylhexanoyl chloride for propionyl anhydride, the following esters of Compound 9 are obtained:

$7\alpha$-methyl-$17_a\beta$-acetyloxy-D-homo-19-norandrost-4,16-dien-3-one;

$7\alpha$-methyl-$17_a\beta$-propionyloxy-D-homo-19-norandrost-4,16-dien-3-one;

$7\alpha$-methyl-$17_a\beta$-n-octanoyloxy-D-homo-19-norandrost-4,16-dien-3-one;

$7\alpha$-methyl-$17_a\beta$-eicosanoyloxy-D-homo-19-norandrost-4,16-dien-3-one;

$7\alpha$-methyl-$17_a\beta$-acryloyloxy-D-homo-19-norandrost-4,16-dien-3-one;

$7\alpha$-methyl-$17_a\beta$-methacryloyloxy-D-homo-19-norandrost-4,16-dien-3-one;

$7\alpha$-methyl-$17_a\beta$-2-tetracosenyloxy-D-homo-19-norandrost-4,16-dien-3-one;

$7\alpha$-methyl-$17_a\beta$-propynoyloxy-D-homo-19-norandrost-4,16-dien-3-one;

$7\alpha$-methyl-$17_a\beta$-2-tetracosynoyloxy-D-homo-19-norandrost-4,16-dien-3-one;

$7\alpha$-methyl-$17_a\beta$-2-chloroacetyloxy-D-homo-19-norandrost-4,16-dien-3-one;

$7\alpha$-methyl-$17_a\beta$-2-chlorotetracosanoyloxy-D-homo-19-norandrost-4,16-dien-3-one;

$7\alpha$-methyl-$17_a\beta$-benzoyloxy-D-homo-19-norandrost-4,16-dien-3-one;

$7\alpha$-methyl-$17_a\beta$-4-chlorobenzoyloxy-D-homo-19-norandrost-4,16-dien-3-one;

$7\alpha$-methyl-$17_a\beta$-4-methylbenzoyl-D-homo-19-norandrost-4,16-dien-3-one;

$7\alpha$-methyl-$17_a\beta$-2-naphthoyloxy-D-homo-19-norandrost-4,16-dien-3-one;

$7\alpha$-methyl-$17_a\beta$-6-bromo-2-naphthoyloxy-D-homo-19-norandrost-4,16-dien-3-one;

$7\alpha$-methyl-$17_a\beta$-phenylacetyloxy-D-homo-19-norandrost-4,16-dien-3-one;

$7\alpha$-methyl-$17_a\beta$-3-phenylpropionoyloxy-D-homo-19-norandrost-4,16-dien-3-one; or $7\alpha$-methyl-$17_a\beta$-6-phenylhexanoyloxy-D-homo-19-norandrost-4,16-dien-3-one.

EXAMPLE 10

The following example illustrates the preparation of representative pharmaceutical formulations containing an active compound of formula I, e.g. $7\alpha$-methyl-$17_a\beta$-propionyloxy-D-homo-19-norandrost-4,16-dien-3-one.

| I.V. Formulation | |
|---|---|
| Active compound | 0.14 g |
| Propylene glycol | 20.0 g |
| POLYETHYLENE GLYCOL 400 | 20.0 g |
| TWEEN 80 | 1.0 g |

| I.V. Formulation | |
|---|---|
| 0.9% Saline solution | 100.0 ml |

In Examples 11 through 17, the active ingredient is $7\alpha$-methyl-$17_a\beta$-propionyloxy-D-homo-19-norandrost-4,16-dien-3-one. Other compounds of formula I may be substituted therein.

EXAMPLE 11

| Ingredients | Quantity per tablet, mgs. |
|---|---|
| Active ingredient | 10 |
| cornstarch | 20 |
| lactose, spray-dried | 153 |
| magnesium stearate | 2 |

The above ingredients are thoroughly mixed and pressed into single scored tablets.

EXAMPLE 12

| Ingredients | Quantity per capsule, mgs. |
|---|---|
| Active ingredient | 5 |
| lactose, spray-dried | 148 |
| magnesium stearate | 2 |

The above ingredients are mixed and introduced into a hard-shell gelatin capsule.

EXAMPLE 13

| Ingredients | Quantity per tablet, mgs. |
|---|---|
| Active ingredient | 0.5 |
| cornstarch | 50 |
| lactose | 145 |
| magnesium stearate | 5 |

The above ingredients are mixed intimately and pressed into single scored tablets.

EXAMPLE 14

| Ingredients | Quantity per capsule, mgs. |
|---|---|
| Active ingredient | 0.1 |
| lactose | 15 |
| cornstarch | 25 |
| magnesium stearate | 2 |

The above ingredients are mixed and introduced into a hard-shell gelatin capsule.

EXAMPLE 15

| Ingredients | Quantity per capsule, mgs. |
|---|---|
| Active ingredient | 10 |
| lactose | 92 |

The above ingredients are mixed and introduced into a hard-shell gelatin capsule.

EXAMPLE 16

An injectable preparation buffered to a pH of 7 is prepared having the following composition:

| Ingredients | |
|---|---|
| Active ingredient | 0.2 g |
| $KH_2PO_4$ buffer (0.4 M solution) | 2 ml |
| KOH (1 N) | q.s. to pH 7 |
| water (distilled, sterile) | q.s. to 20 ml |

EXAMPLE 17

An oral suspension is prepared having the following composition:

| Ingredients | | |
|---|---|---|
| Active ingredient | 0.1 | g |
| fumaric acid | 0.5 | g |
| sodium chloride | 2.0 | g |
| methyl paraben | 0.1 | g |
| granulated sugar | 25.5 | g |
| sorbitol (70% solution) | 12.85 | g |
| Veegum K (Vanderbilt Co.) | 1.0 | g |
| flavoring | 0.035 | ml |
| colorings | 0.5 | mg |
| distilled water q.s. to | 100 | ml |

The compounds of this invention are characterized by having signifigant oral androgenic activity. Compounds of the invention were tested for androgenic activity using the oral Hershberger test and the subcutaneous Hershberger test. In addition, the conpounds were examined using a receptor binding assay (RBA). Normally potent androgens have a high RBA value and materials with low RBA's have low activity. The resuts so obtained were compared with results listed in publications and patents for other androgenic materials. To facilitate comparison, all values were compared to 17α-methyl testosterone which was arbitrarily assigned a value of 1.0 for oral and subcutaneous androgenic activity. The results of this comparison are given in Table 1 and show that the compounds of this invention have markedly higher oral activity than any other norandrostone materials. The only other material having similar activity being a the testosterone material of Segaloff. These results also point out another unexpected property of the present compounds. While they do have outstanding oral activity, they give very low values for receptor binding. Thus, the usual predictor of activity suggests that the present compounds would be inactive, but instead they are extemely active. Finally, a compound disclosed by Furth et al in U.S. Pat. No. 4,155,918 is seen to have a much lower activity than the presently claimed materials.

TABLE 1

| COMPOUND | ANDROGENIC ACTIVITY(RAT) | | |
|---|---|---|---|
| | ORAL | SUBQ | RBA |
| Compounds of this invention [structure with OCCH2CH3] | 5 | 40 | 8% |
| [structure with OH] | 4 | 20–40 (Est) | 2% |
| Testosterone | 0.03 | 1 | 20% |
| 17-Methyltestosterone | 1 | 1 | 40% |
| Dihydrotestosterone | 0.1 | | 100% |
| Segaloff Compound [structure with OH] | 5.7 | 100± | — |
| Segaloff Compound [structure with OC(CH2)3CH3] | 2.5 | 20 | |
| Furst Compound | Not shown | 3 | |
| Other Compounds [structure with OCCH2CH3] | 0.2 | 4 | |

TABLE 1-continued

| COMPOUND | ANDROGENIC ACTIVITY(RAT) | | |
|---|---|---|---|
| | ORAL | SUBQ | RBA |
| 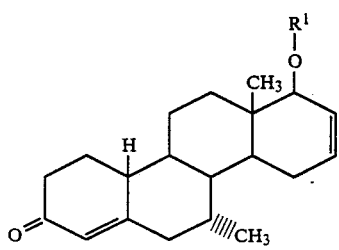 | 0.1 | 40 | |
| 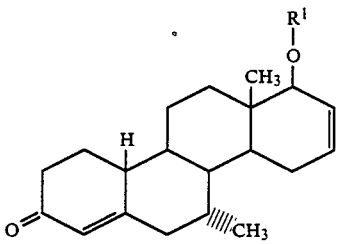 | 0.2 | 3 | |

While the present invention has been described with reference to the specific embodiments thereof, it should be understood by those skilled in this art that various changes may be made and equivalents may be substituted without departing from the true spirit and scope of the invention.

What is claimed is:

1. A compound of the formula

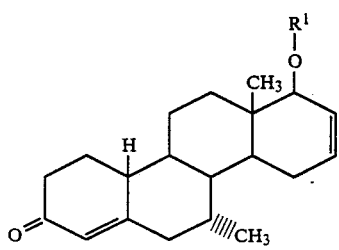

wherein $R^1$ is hydrogen or an acyl of the formula

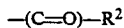

wherein $R^2$ is an organic substituent selected from the group consisting of a 1 to 24 carbon atom alkyl, a 2 to 24 carbon atom alkenyl, a 2 to 24 carbon atom alkynyl, a 3 to 8 carbon atom cycloalkyl, a 4 to 32 carbon atom cycloalkylalkylene, a 1 to 24 carbon atom haloalkyl, phenyl or 1 or 2 naphthyl aryl containing up to 4 one to six carbon atom alkyl substituents, a halophenyl and a halonaphthyl each containing up to 4 one to six carbon atom alkyl substituents, and an aralkyl made up of a 1 to 6 carbon atom alkyl substituted with a phenyl or a naphthyl each containing from 0 to 4 one to six carbon atom alkyls.

2. The compound of claim 1 wherein $R^1$ is hydrogen.

3. The compound of claim 1 wherein $R^1$ is acyl and $R^2$ is selected from the group consisting of a 1 to 24 carbon atom alkyl, a 2 to 24 carbon atom alkenyl, a 2 to 24 carbon atom alkynyl, a 3 to 8 carbon atom cycloalkyl, a 4 to 32 carbon atom cycloalkylalkylene, phenyl or 1 or 2 naphthyl aryl containing up to 4 one to six carbon atom alkyl substituents, and an aralkyl made up of a 1 to 6 carbon atom alkyl substituted with a phenyl or a naphthyl each containing from 0 to 4 one to six carbon atom alkyls.

4. The compound of claim 3 wherein $R^1$ is acyl and $R^2$ is alkyl of 1 to 16 carbon atoms.

5. The compound of claim 4 wherein $R^1$ is acyl and $R^2$ is ethyl.

6. The compound of claim 4 wherein $R^1$ is acyl and $R^2$ is n-hexyl.

7. The compound of claim 4 wherein $R^1$ is acyl and $R^2$ is n-nonyl.

8. A pharmaceutical composition useful by oral administration for control of fertility in a male mammal while maintaining the male libido which comprises an effective fertility controlling amount of a compound of claim 1 in admixture with a pharmaceutically acceptable oral excipient.

9. A pharmaceutical composition useful by oral administration for producing an androgenic response in a male mammal which comprises an effective androgenic response producing amount of a compound of the formula

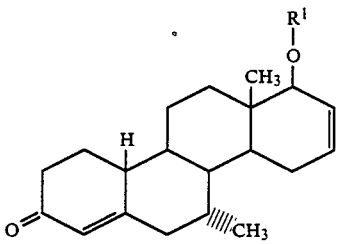

wherein $R^1$ is hydrogen or an acyl of the formula

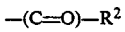

wherein $R^2$ is an organic substituent selected from the group consisting of a 1 to 24 carbon atom alkyl, a 2 to 24 carbon atom alkenyl, a 2 to 24 carbon atom alkynyl, a 3 to 8 carbon atom cycloalkyl, a 4 to 32 carbon atom cycloalkylalkylene, a 1 to 24 carbon atom haloalkyl, phenyl or 1 or 2 naphthyl aryl containing up to 4 one to six carbon atom alkyl substituents, a halophenyl and a halonaphthyl each containing up to 4 one to six carbon atom alkyl substituents, and an aralkyl made up of a 1 to 6 carbon atom alkyl substituted with a phenyl or a naphthyl each containing from 0 to 4 one to six carbon atom alkyls, in admixture with a pharmaceutically acceptable oral excipient.

10. The pharmaceutical composition of claim 9 wherein $R^1$ is hydrogen or an acyl in which $R^2$ is ethyl.

11. A pharmaceutical composition useful by oral administration for control of fertility in a male mammal while maintaining the male libido which comprises an effective fertility controlling amount of LHRH antagonist and an effective androgenic response producing amount of a compound of the formula

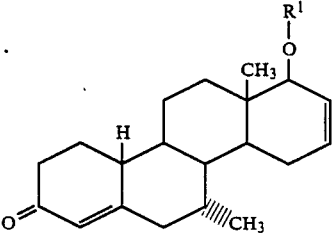

wherein $R^1$ is hydrogen or an acyl of the formula

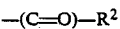

wherein R² is an organic substituent selected from the group consisting of a 1 to 24 carbon atom alkyl, a 2 to 24 carbon atom alkenyl, a 2 to 24 carbon atom alkynyl, a 3 to 8 carbon atom cycloalkyl, a 4 to 32 carbon atom cycloalkylalkylene, a 1 to 24 carbon atom haloalkyl, phenyl or 1 or 2 naphthyl aryl containing up to 4 one to six carbon atom alkyl substituents, a halophenyl and a halonaphthyl each containing up to 4 one to six carbon atom alkyl substituents, and an aralkyl made up of a 1 to 6 carbon atom alkyl substituted with a phenyl or a naphthyl each containing from 0 to 4 one to six carbon atom alkyls, in admixture with a pharmaceutically acceptable oral excipient.

12. The pharmaceutical composition of claim 11 wherein R¹ is hydrogen or an acyl in which R² is ethyl.

13. A method for decreasing fertility in a male mammal comprising administering to the mammal an effective spermatogenesis decreasing amount of a compound of the formula

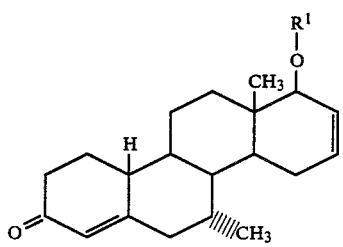

wherein R¹ is hydrogen or an acyl of the formula

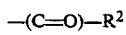

wherein R² is an organic substituent selected from the group consisting of a 1 to 24 carbon atom alkyl, a 2 to 24 carbon atom alkenyl, a 2 to 24 carbon atom alkynyl, a 3 to 8 carbon atom cycloalkyl, a 4 to 32 carbon atom cycloalkylalkylene, a 1 to 24 carbon atom haloalkyl, phenyl or 1 or 2 naphthyl aryl containing up to 4 one to six carbon atom alkyl substituents, a halophenyl and a halonaphthyl each containing up to 4 one to six carbon atom alkyl substituents, and an aralkyl made up of a 1 to 6 carbon atom alkyl substituted with a phenyl or a naphthyl each containing from 0 to 4 one to six carbon atom alkyls.

14. The method of claim 13 wherein the mammal is a human being and the effective spermatogenesis decreasing amount is from 1 to 10 mg/kg/day.

15. The method of claim 14 wherein R¹ is an acyl in which R² is ethyl.

16. A method for increasing fertility in a male mammal comprising administering to the mammal an effective spermatogenesis increasing amount of a compound of the formula

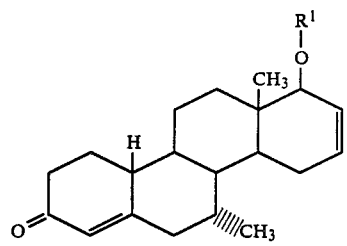

wherein R¹ is hydrogen or an acyl of the formula

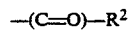

wherein R² is an organic substituent selected from the group consisting of a 1 to 24 carbon atom alkyl, a 2 to 24 carbon atom alkenyl, a 2 to 24 carbon atom alkynyl, a 3 to 8 carbon atom cycloalkyl, a 4 to 32 carbon atom cycloalkylalkylene, a 1 to 24 carbon atom haloalkyl, phenyl or 1 or 2 naphthyl aryl containing up to 4 one to six carbon atom alkyl substituents, a halophenyl and a halonaphthyl each containing up to 4 one to six carbon atom alkyl substituents, and an aralkyl made up of a 1 to 6 carbon atom alkyl substituted with a phenyl or a naphthyl each containing from 0 to 4 one to six carbon atom alkyls.

17. The method of claim 16 wherein the mammal is a human being and the effective spermatogenesis increasing amount is from 0.01 to 0.99 mg/kg/day.

18. The method of claim 17 wherein R¹ is an acyl in which R² is ethyl.

19. A method for achieving an androgenic response in a male mammal comprising orally administering to the mammal an effective oral androgenic response producing amount of a compound of the formula

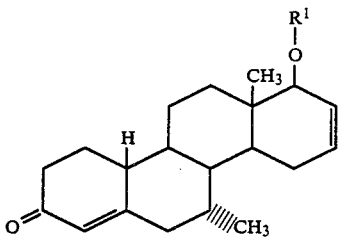

wherein R¹ is hydrogen or an acyl of the formula

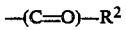

wherein R² is an organic substituent selected from the group consisting of a 1 to 24 carbon atom alkyl, a 2 to 24 carbon atom alkenyl, a 2 to 24 carbon atom alkynyl, a 3 to 8 carbon atom cycloalkyl, a 4 to 32 carbon atom cycloalkylalkylene, a 1 to 24 carbon atom haloalkyl, phenyl or 1 or 2 naphthyl aryl containing up to 4 one to six carbon atom alkyl substituents, a halophenyl and a halonaphthyl each containing up to 4 one to six carbon atom alkyl substituents, and an aralkyl made up of a 1 to 6 carbon atom alkyl substituted with a phenyl or a naphthyl each containing from 0 to 4 one to six carbon atom alkyls.

20. The method of claim 19 wherein the mammal is a human being and the effective oral androgenic response producing amount is from 0.02 to 1 mg/kg/day.

21. The method of claim 20 wherein R¹ is an acyl in which R² is ethyl.

* * * * *

UNITED STATES PATENT AND TRADEMARK OFFICE
CERTIFICATE OF CORRECTION

PATENT NO. : 4,788,218

DATED : Nov. 29, 1988

INVENTOR(S) : Masato Tanabe et al.

It is certified that error appears in the above-identified patent and that said Letters Patent is hereby corrected as shown below:

On cover page 1, column 1, line 8, under the heading "Inventors", please delete "Peters, Richard H., both of San Jose; Mitchell A.g34 Avery, Palo Alto, all of Calif." and insert therefor --Richard H. Peters, both of San Jose; Mitchell A. Avery, Palo Alto, all of Calif.--.

Signed and Sealed this

Eleventh Day of April, 1989

Attest:

DONALD J. QUIGG

*Attesting Officer*

*Commissioner of Patents and Trademarks*